United States Patent
Markus et al.

(10) Patent No.: US 11,819,400 B2
(45) Date of Patent: Nov. 21, 2023

(54) METHOD AND APPARATUS FOR AN ADAPTIVE FOCUS LENS

(71) Applicant: EP Global Communications, Inc., Irvine, CA (US)

(72) Inventors: David T. Markus, Irvine, CA (US); Michael C. Hayes, Irvine, CA (US); Arthur Back, Pleasanton, CA (US)

(*) Notice: Subject to any disclaimer, the term of this patent is extended or adjusted under 35 U.S.C. 154(b) by 0 days.

(21) Appl. No.: 15/525,286

(22) PCT Filed: Nov. 3, 2015

(86) PCT No.: PCT/US2015/058783
§ 371 (c)(1),
(2) Date: May 8, 2017

(87) PCT Pub. No.: WO2016/073446
PCT Pub. Date: May 12, 2016

(65) Prior Publication Data
US 2018/0284482 A1    Oct. 4, 2018

Related U.S. Application Data

(60) Provisional application No. 62/077,097, filed on Nov. 7, 2014.

(51) Int. Cl.
| | | |
|---|---|---|
| A61F 2/14 | (2006.01) | |
| G02C 7/02 | (2006.01) | |
| G02C 7/04 | (2006.01) | |
| G02B 3/14 | (2006.01) | |
| G02C 7/08 | (2006.01) | |
| A61F 2/16 | (2006.01) | |
| G02B 26/08 | (2006.01) | |

(52) U.S. Cl.
CPC .......... *A61F 2/1451* (2015.04); *A61F 2/1635* (2013.01); *G02B 3/14* (2013.01); *G02B 26/0875* (2013.01); *G02C 7/04* (2013.01); *G02C 7/081* (2013.01); *A61F 2002/1681* (2013.01)

(58) Field of Classification Search
CPC . G02C 7/02; G02C 7/04; G02C 7/081; G02B 3/12; G02B 3/14; A61F 2/1451; A61F 2/1635
USPC .............. 351/159.03, 159.34, 159.39, 159.4, 351/159.68
See application file for complete search history.

(56) References Cited

U.S. PATENT DOCUMENTS 5,171,266 A * 12/1992 Wiley .................. A61F 2/1613
                                                   623/6.22
5,800,530 A *  9/1998 Rizzo, III ............. A61F 2/1613
                                                   623/6.22

(Continued)

*Primary Examiner* — Darryl J Collins
(74) *Attorney, Agent, or Firm* — Kafantaris Law Offices; Theo Kafantaris

(57) ABSTRACT

Methods and apparatus are provided for adaptively focusing a lens. In one approach, electromagnetic energy is employed to modify a shape or thickness of a lens such that its refractive power and focal length are modified. In one aspect, a lens embodying adaptive focus features requires low power, and can be adjusted quickly. One or a plurality of electromagnets can be employed to compress or separate end portions of an embedded haptic, the force from which acts to alter the shape of the haptic, thus modifying the refractive power and focal length of a lens.

15 Claims, 15 Drawing Sheets

(56) References Cited

U.S. PATENT DOCUMENTS

| | | | |
|---|---|---|---|
| 2003/0147046 A1* | 8/2003 | Shadduck | A61F 2/1613 351/159.69 |
| 2009/0033863 A1* | 2/2009 | Blum | A61F 2/14 351/159.34 |
| 2011/0149410 A1* | 6/2011 | Blum | G02B 3/14 359/666 |

* cited by examiner

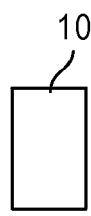 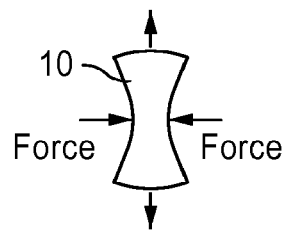 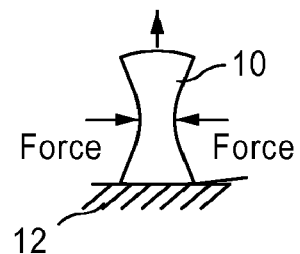
Fig. 1A  Fig. 1B  Fig. 1C
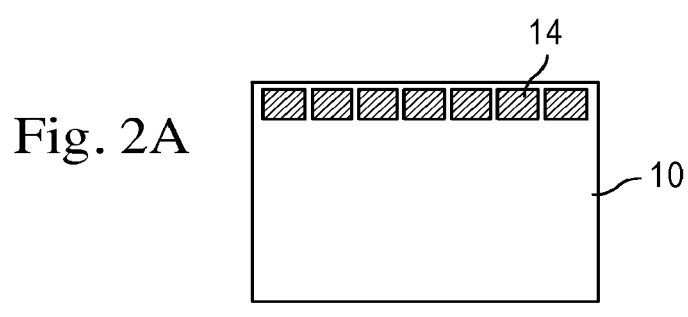
Fig. 2A
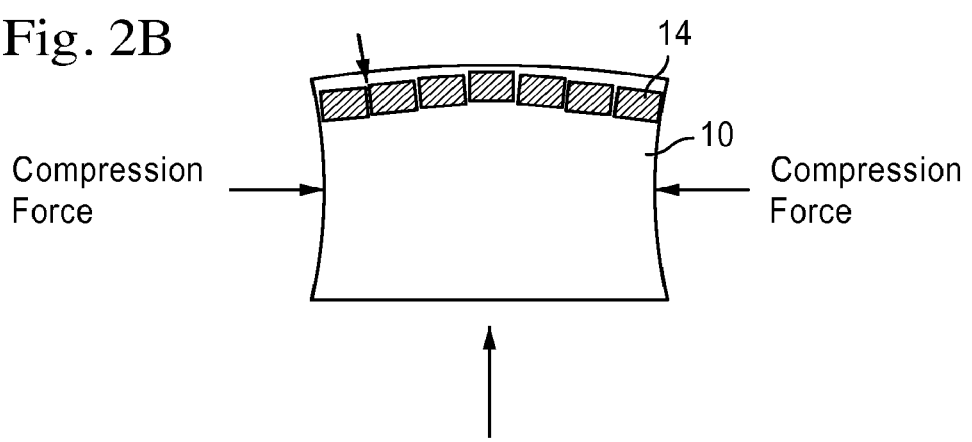
Fig. 2B

METHOD AND APPARATUS FOR AN ADAPTIVE FOCUS LENS

CROSS-REFERENCE TO RELATED APPLICATIONS

This application claims the benefit of PCT/US15/58783, filed on Nov. 3, 2015, which claims the benefit of U.S. Provisional Patent Application No. 62/077,097, filed on Nov. 7, 2014, both of which are incorporated herein by reference.

STATEMENT REGARDING FEDERALLY SPONSORED RESEARCH AND DEVELOPMENT

Not Applicable.

FIELD OF THE INVENTION

The present disclosure is directed to adaptively tuning a lens, and more particularly, to methods and apparatus for electromagnetically adjusting the power and focal point of a lens.

DISCUSSION OF RELATED ART

A lens can generally be described as a device made from glass or other transparent material adapted to refract light. Conventionally, lenses have fixed focal properties and are manufactured for specific purposes. For example, eyeglasses and contact lenses are examples of lenses configured to provide vision correction by converging the light onto the eyes. A magnifying glass is an example of a lens configured to enlarge a target area visually by converging the light passing through the area into a beam. Telescopes, cameras, microscopes, and projectors all utilize lenses to provide their specific utility.

An adaptive lens can generally be described as a lens having adaptive focal properties. One primary example of an adaptive lens is a zoom lens, where the focal length of the lens is variable. Typically, an adaptive lens will either physically displace a lens or displace a plurality of lenses or lens elements for adjusting the focal length. Furthermore, each individual lens may converge or diverge the light such that, when displaced, they provide zooming or magnification.

Contact lenses are generally thin and light devices adapted to temporarily attach to the eyes for providing refractive error correction. There are two common types of contact lenses, hard lenses and soft lenses. Soft lenses are typically made from hydrogel or silicone hydrogel, which allow them to, flex, expand and contract, making them more comfortable for daily use. Benefits to lens wearers associated with silicone hydrogel contact lenses can be attributed, at least in part, to the combination of hydrophilic components and the hydrophobic properties of silicon-containing polymeric materials of the contact lenses.

While current contact lenses are configured to provide vision correction, more attention can be been paid to providing lenses with an ability to adaptively adjust power and focal length. Adaptively adjusting power and focal length also has important applications in other medical and non-medical arts, and particularly in connection with intra-ocular lenses, inlays, onlays, endoscopes, and in fiber optics Accordingly, there is a continued need for approaches to adaptively modify the power, focal length, light intensity, and zoom of lenses. The present disclosure satisfies these and other needs.

SUMMARY OF THE INVENTION

Briefly, and in general terms, the present disclosure is directed towards methods and apparatus for adaptively modifying the power and focal length of lenses, and of contact lenses in particular. Furthermore, there are provided approaches to adaptively adjust curvature and/or thickness of lenses. This can be accomplished by associating or embedding a haptic capsule with or within a lens, wherein the haptic capsule embodies a flexible shape and provides a lens with desired adaptive focal properties.

In one particular approach, electromagnetic energy is employed to modify the shape of a haptic associated with a lens such that its refractive power and focal length are modified through the controlled alteration of curvature and/or thickness of the lens. Furthermore, the contemplated approach requires low power, and can be adjusted quickly. This can be accomplished by utilizing one or a plurality of electromagnets to compress or separate the end portions or other portions of a haptic. The electromechanical force from each electromagnet will alter the shape of the haptic changing the thickness and/or curvature of a portion of the lens, thus modifying refractive power and focal length of the lens.

A haptic configured for inclusion with a lens can be flexible or rigid, and can embody material that can change curvature or shape in response to an applied force. The haptic can be formed of the same or different material than the lens into which it is incorporated. In the context of a contact lens, the haptic can be made from the same or different material than the remainder of the contact lens, and the material surrounded or bounded by the haptic can embody the same or different material from remaining portions of the lens. Further, the haptic can be assembled prior to embedding within a lens and retained within the lens during further processing and manufacturing, or the haptic can be formed along with the creation of the lens. Moreover, the haptic can assume a myriad of shapes, and embody various features. In one aspect, the haptic can be transparent and can have the same or similar refractive index as material surrounding the haptic. In other aspects, the haptic can be rotationally symmetric or asymmetric, or it can assume omega, square, oval, elliptical or other shapes, define a generally ribbon shape with overlapping ends, or define other configurations where endpoints, portions or gaps can be manipulated via applied forces to change the shape of the haptic. The haptic can also have or assume variable dimensions including thicknesses, as well as angular or angled portions, and discontinuous patterns.

It is further contemplated that a haptic adapted for incorporation into a lens can be configured to bound an area that is occupied by one or more of a polymer or other flexible solid, air or fluid, or combinations thereof, as well as partitions or segments. Such bounded material or area is to be sufficiently flexible to provide desired curvature or thickness adjustments. One or a plurality of haptics can be incorporated within a lens to achieve the desired effect, and each of concentrically arranged, overlapping, arrays, and discrete placement of one or varied sizes of haptics are contemplated. Additionally, one or more haptics can define a discontinuous structure including a single gap between adjacent end portions, or there can be multiple breaks and gaps formed in the haptic, each of which is configured to change the structure responsive to electromagnetic energy. One or more haptics can also be planar or non-planar, and one or more haptics can be embedded at various angles within a lens.

Additional embodiments and aspects of the disclosure will be apparent from the following description, drawings, and claims. As can be appreciated from the foregoing and following description, each and every feature described herein, and each and every combination of two or more of such features, and each and every combination of one or more values defining a range, are included within the scope of the present disclosure provided that the features included in such a combination are not mutually inconsistent.

In addition, any feature or combination of features or any value(s) defining a range may be specifically excluded from any embodiment of the present disclosure.

DESCRIPTION OF THE DRAWINGS

Embodiments of this invention may best be understood by referring to the following description and accompanying drawings that are used to illustrate the invention. In the drawings:

FIG. 1A is a simplified cross-sectional view of a mold useful for forming a swellable contact lens, as an example of a swellable medical device;

FIGS. 1A-C depict an elastic component, and forces being applied thereto;

FIGS. 2A-E depict an elastic component with energy blocking components, and the modification thereof upon the application of a force to the elastic component;

DETAILED DESCRIPTION OF THE PREFERRED EMBODIMENT

Embodiments of the present disclosure are described herein in the context of an adaptive focus lens. Although the present disclosure is sometimes exemplified in the context of a medical device, it will be understood that the present disclosure relates to contact lenses as well as non-medical arts.

Those of ordinary skill in the art will realize that the following detailed description of the present disclosure is illustrative only and is not intended to be in any way limiting. Other embodiments of the present disclosure will readily suggest themselves to such skilled persons having the benefit of this disclosure. Reference will now be made in detail to implementations of the present disclosure as illustrated in the accompanying drawings.

The same reference indicators will be used throughout the drawings and the following detailed description to refer to the same or like parts.

The present disclosure provides methods and apparatus for adaptively focusing a lens. Specifically, there is disclosed a method and apparatus for electromagnetically modifying the shape, curvature or thickness of an elastic lens such that its refractive power and focal length are modified. Furthermore, the present approach requires low power, can be adjusted quickly (low hysteresis), can be made from any flexible material (silicone hydrogel) or flexible polymer, utilizes digital control (on or off), and may be incorporated into the elastic material of a contact lens and also in other miniaturization, soft and flexible lens applications.

Figure 2C:
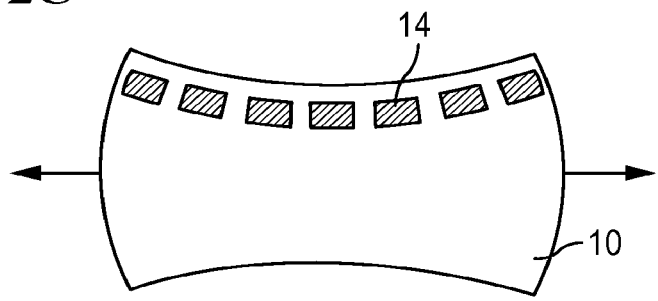
Figure 2D:
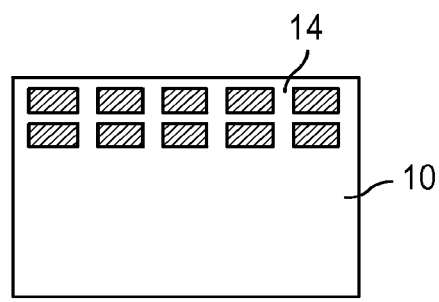
Figure 2E:
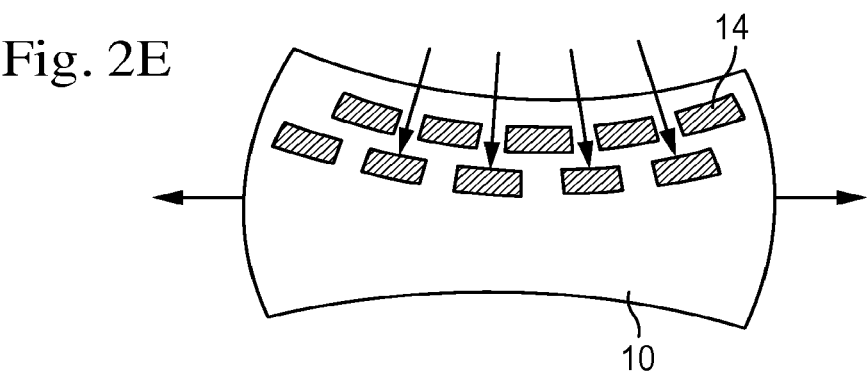

With reference to FIGS. 1A-D and 2A-B, there are presented various characteristics of an elastic material 10. When opposing forces are applied to opposite sides of an elastic material 10 as shown in FIG. 1A, the elastic material 10 will narrow at the point of contact with the applied forces, and will expand in directions orthogonal to the applied forces. Where there is adhesion of a complete end surface of one end of the elastic material to a more rigid piece 12 for example, the elastic material will narrow at the point of contact of the force and expand in one or more directions away from the rigid piece 12. Further, such elastic material 10 can include light or energy blocking elements 14 which can be manipulated upon the application of forces to and changing shape of the elastic material 10. As shown in FIG. 2A, the blocking elements 14 are aligned such that energy cannot pass. When forces are applied to the elastic material as shown in FIG. 2B, the blocking elements 14 change relative positioning and provide spaces therebetween for light or energy to pass. Many further applications are also envisaged including controlling energy delivery very precisely, light filtering, and polymerization control with different stretch levels. Further possible examples are depicted in FIGS. 2C-D. That is, tensile forces can be placed upon the elastic material 10 shown in FIGS. 2A-B, thus producing a different pattern of the blocking elements 14 and consequently a different energy transmission through the elastic material 10. Various rows and columns of aligned or staggered blocking elements 14 can also be employed to create other energy transmission characteristics or profiles such as that shown in FIGS. 2D-E, for example.

Figure 3A:
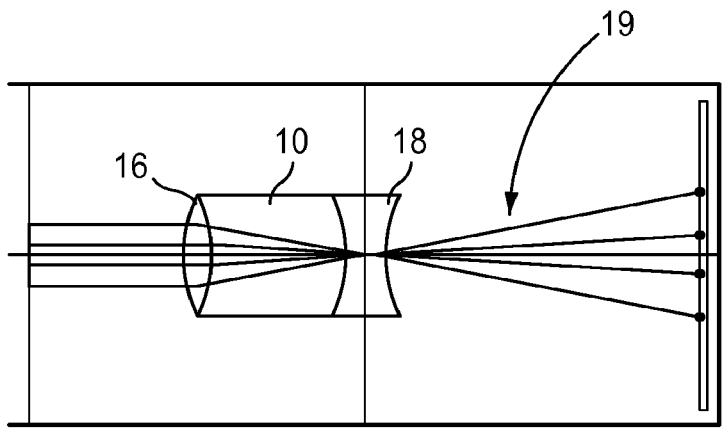
FIGS. 3A-C depict an elastic component placed between a pair of lenses, and the effect on focal length when varying forces are applied to the elastic component.
Figure 3B:
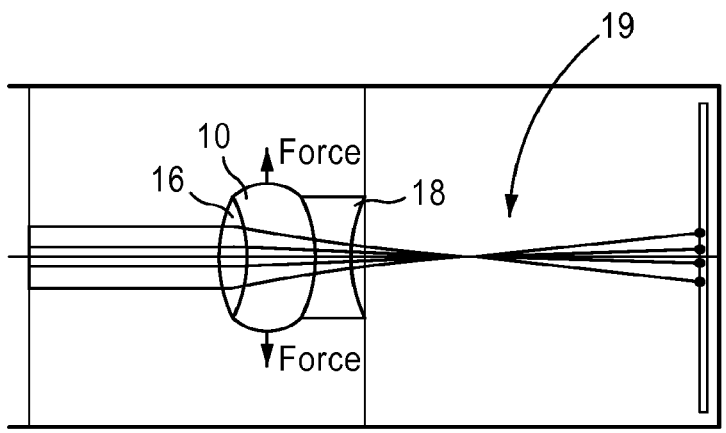
Figure 3C:
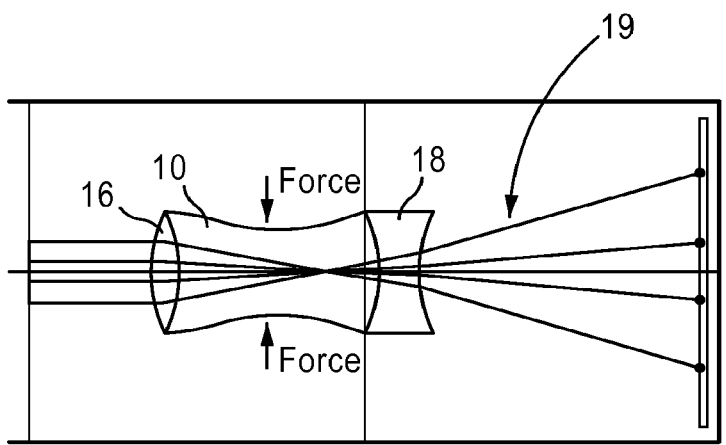
Figure 3D:
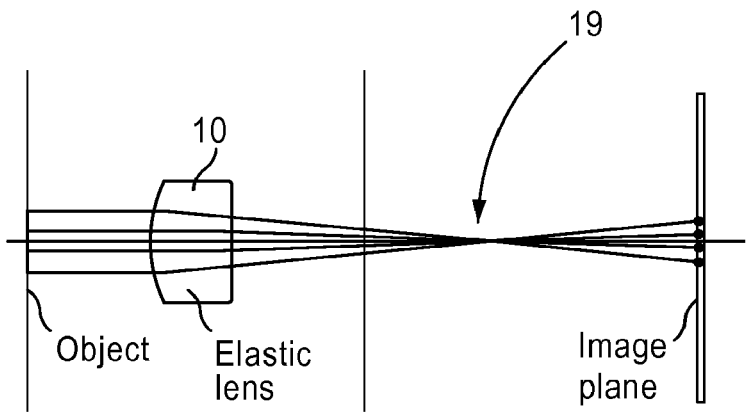
FIGS. 3D-E depict an elastic component in the form of an elastic lens, and the effect when a forces is applied thereto.
Figure 3E:
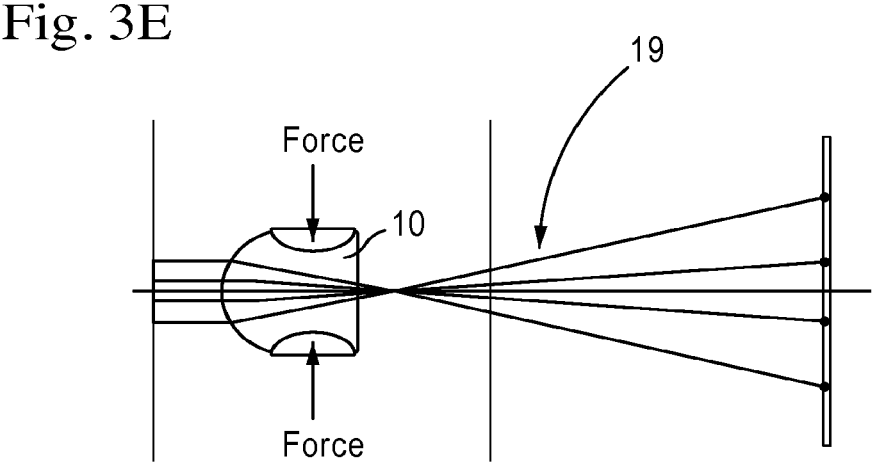

With reference to FIGS. 3A-C, elastic material 10 also can be placed between lenses having varying shapes, and can thus have an effect on light passing through the assemblies. Although shown as being placed between one convex 16 and one concave 18 lens, the elastic material 10 can also be placed between the same types of lenses, or can be placed between other lens types such as spherical, aspheric, toric or multi-focal or other lens types, or in optical configurations that impact light travel based on how a haptic is deformed. In any event, as depicted in FIGS. 3B and C, tensile or compressive forces can be placed upon the elastic material 10 to change the shape of the elastic material 10. Tensile forces cause the elastic material 10 to compress or contract, thereby providing a more narrow space for light to pass orthogonally to the lenses 16, 18. Compressive forces have an opposite effect, causing the elastic material 10 to expand in the direction light passes orthogonally to the lenses 16, 18. In this way, as shown by the through the assemblies can be controlled by deforming the elastic material 20. This of course has potential applications to adaptively tuning a lens assembly in medical or non-medical arts. As shown in FIGS. 3D-E, these effects can be produced where the elastic material 10 itself defines a lens without other lenses attached thereto. Here, the curvature change through the deformation of the elastic material 10 can be utilized to have a desired effect on light as it passes through the elastic material 10, as illustrated by the ray traces 19.

Figure 4A:
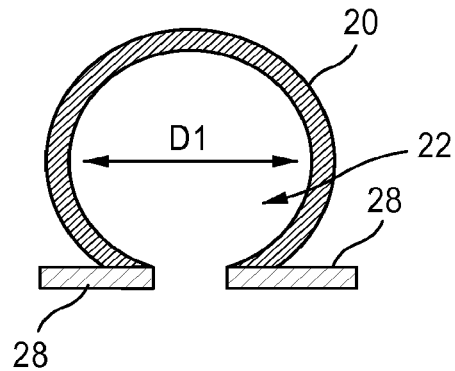
FIGS. 4A-C are front views, depicting one configuration of a haptic.
Figure 4B:
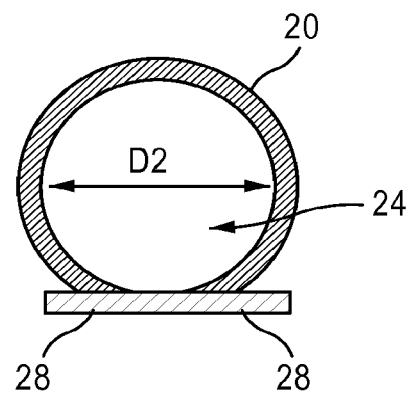
Figure 4C:
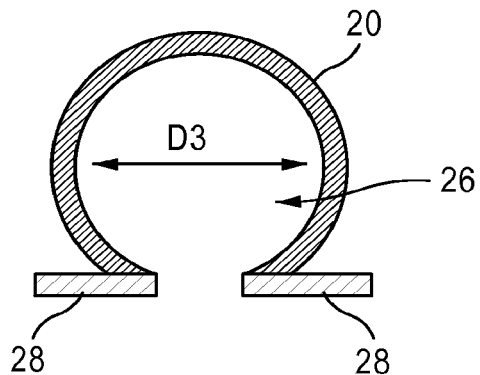
Figure 4D:
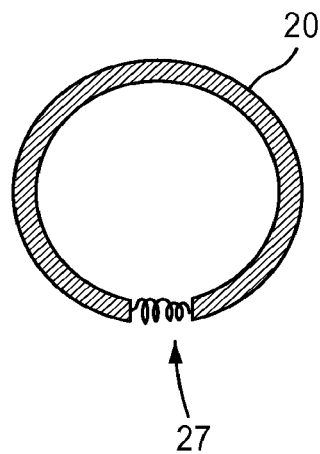
FIGS. 4D-E are front views, depicting alternative configurations of a haptic
Figure 4E:
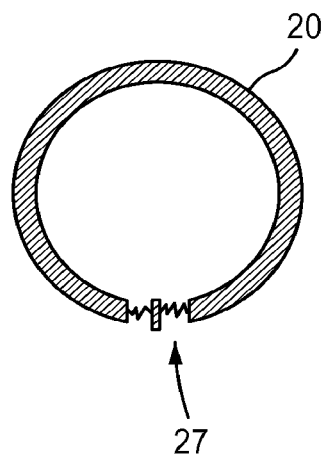

Turning to FIGS. 4A-C, there is shown one example of a structure which can be configured to accomplish the application of effective compressive forces or effective tensile, or rather outwardly directed, forces to elastic material as shown in FIGS. 3A-C. Here, such structure can assume a general omega shape 20, and can assume an open configuration 22 having a diameter D1 (FIG. 4A), a closed configuration 24 having a relatively smaller diameter D2 (FIG. 4B), and an open wide configuration 26 having a diameter D3 (FIG. 4C), which is larger than D1. In the context of an embedded component within or otherwise associated with a lens, this structure is referred to below as a haptic, or haptic capsule. Also explained further below, it is to be appreciated that a myriad of various shapes in addition to an omega are contemplated, each of the alternate structures being flexible to change shape and provide desired effects on a lens. It is additionally contemplated that the haptic 20 can assume three states: an open state, a closed state, and a rest state. As such, each state is associated with a unique omega diameter D1, D2, or D3, respectively. In the open state, the end portions 28 are separated, causing curvature and/or thickness to decrease and the power to become less positive as the diameter of the contact lens portion D3 bounded by the haptic 20 increases. In the closed state, the end portions 28 are compressed, causing the curvature and/or thickness to increase and the power of the lens portion D2 bounded by the haptic 20 to become more positive. In the rest state, no force is applied to the end portions 28, and as such, the diameter of the lens portion D1 remains at its predetermined value. In all circumstances, D3>D1>D2. In alternative embodiments, it is contemplated that any number of states may be used. Moreover, as developed further below, various other approaches to the haptic are contemplated. That is, in certain approaches, rather than there being a gap between end portions of an omega patterned haptic, as shown in FIGS. 4D-E, springs or other expandable or flexible structures 27 can span one or more portions of the haptic 20. When placed or embedded within flexible material (not shown) the omega (or other patterned) structure 20 can be caused to change from an open configuration to the closed configuration 24, which results in an effective compressive force being applied to the elastic material 10 (See FIG. 3C). The omega structure 20 can also be positioned to cause a change from the open 22 or closed 24 configuration to the open wide configuration 26 to thereby result in an effective tensile force to be applied to the elastic material (See FIG. 3B). Again, such modification of a lens assembly can be controlled to adaptively tune a lens assembly into which the haptic is incorporated.

Figure 5A:
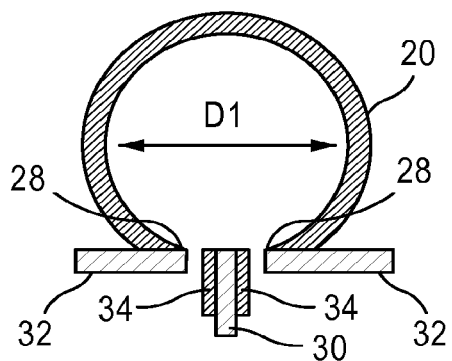
FIGS. 5A-B are front views, depicting flexible structure configured with energy activatable structure in the form of an electromagnet.
Figure 5B:
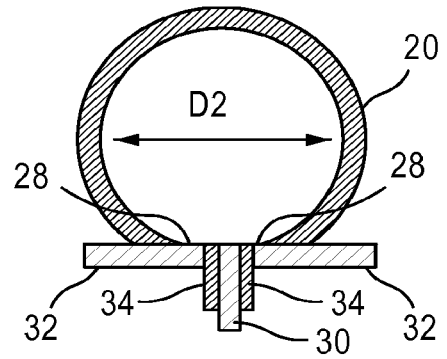

To accomplish modifying the shape of the omega structure 20, in one approach, end portions 28 of the omega (or other) structure can be compressed or separated by one or a plurality of electromagnets 30 (See FIG. 5A-B). The electromechanical force from each electromagnet 30 will alter the shape of the omega structure 20, thus modifying the refractive power and focal length of the lens assembly into which it is incorporated. In one embodiment, each end portion 28 of the omega 20 is configured with a magnet 32. Between each magnet 32 is positioned the electromagnet 30 bounded on opposite sides by metal components 34. In a two state system, activating the electromagnet 30 with power causes the magnets 32 to repel from the metal components 34. Once power is turned off, the omega structure 20 remains open. Activating the electromagnet 30 again causes the metal components 34 to attract the magnets 32 forming the end portions 28, thus closing the omega structure 20. Power is again turned off and the omega structure 20 remains in a closed configuration. As is appreciated by one of ordinary skill in the art, current is manipulated to achieve the desired repelling and attracting action.

Figure 6A:
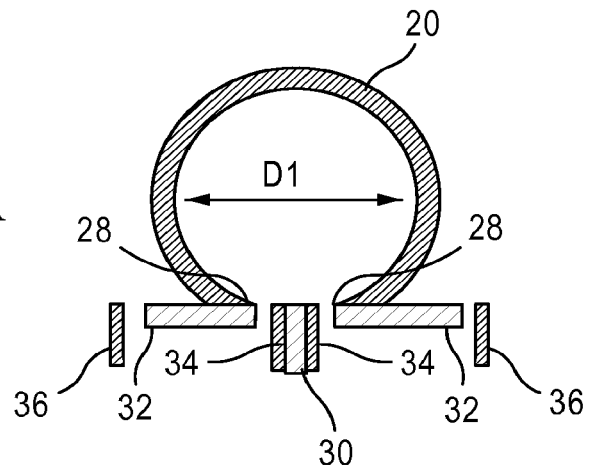
FIGS. 6A-C are front views, depicting an alternative approach to flexible structures configured with an electromagnet and assuming open, closed, and rest states.
Figure 6B:
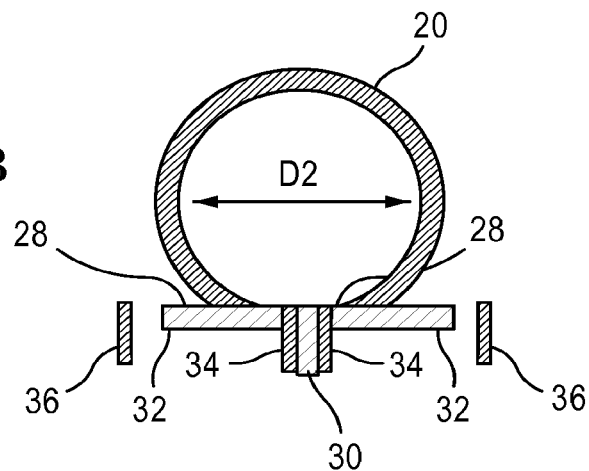
Figure 6C:
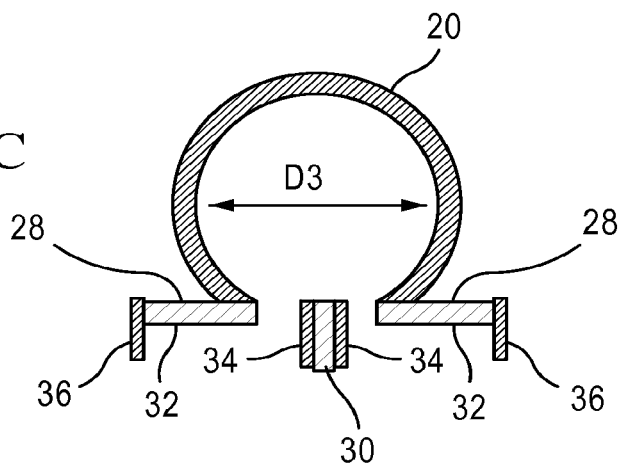

In an alternative three state approach as shown in FIGS. 6A-C, additional metal side components 36 are added to the system. In an open state (FIG. 6A), the electromagnet 30 is activated to repel the magnets 32 forming the end portions of the omega (or other) structure 32. The power to the electromagnet 30 can then be turned off leaving the omega structure 32 to remain open. To accomplish a closed state, the electromagnet can be activated again to attract the magnets 32 to the metal 34 attached to the electromagnet 30. Turning off power thereafter leaves the omega structure 30 in the closed state. Once again activating the electromagnet 30 to a particular selected degree will cause the magnets 32 to repel from the metal attached to the electromagnet and to further cause the magnets 32 to attach to the metal side components 36, where they will remain until the electromagnet is once again activated, thus placing the omega structure in an open wide state.

In one particular aspect, there is contemplated methods and apparatus for adaptively modifying the power and focal length of lenses. In one preferred embodiment, a flexible haptic capsule is embedded within or associated with a contact lens and electromagnetic energy is employed to modify the shape of the haptic such that contact lens refractive power and focal length are modified through the controlled modification of curvature and/or thickness of the lens. As discussed above this can be accomplished by utilizing one or a plurality of electromagnets to compress or separate the end portions or other portions of a haptic. The electromechanical force from an electromagnet will modify the shape of the haptic, thus modifying the polymer or other substance the haptic acts upon and thus changes the refractive power and focal length of the lens.

The term "contact lens" as used herein refers to an ophthalmic lens which, after its removal from a mold in which it is made, is of a structure, size, shape and power that it can be worn on the cornea of an eye. The term "contact lens" can also be understood to refer to an article which upon removal from a mold needs to be treated for example, hydrated and swelled into a lens of size, shape and power as to be wearable on an eye.

Preferably, the contact lens can be a hydrogel-containing lens, more preferably a silicon hydrogel-containing lens.

Figure 7A:
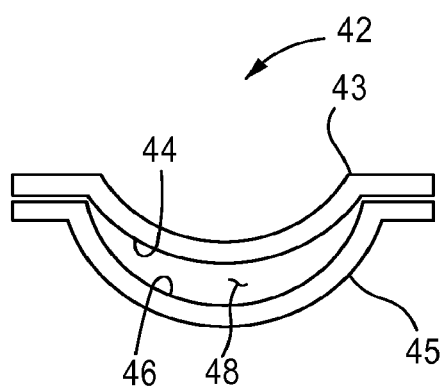
FIGS. 7A-B are cross-sectional views, depicting a conventional approach to contact lens molds.
Figure 7B:
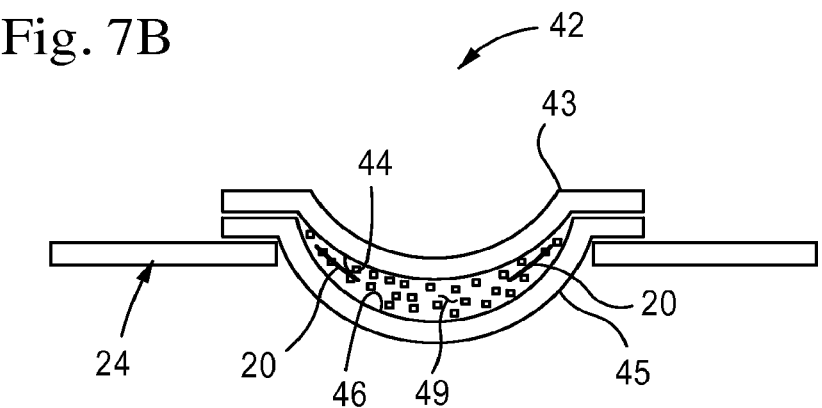

In a broad aspect, methods of manufacturing ophthalmic lenses, for example but not limited to soft silicon hydrogel lenses, are provided. Referring to FIGS. 7A-B, the methods generally include providing a mold assembly 42, such as the mold assembly 42 shown in cross sectional. The mold assembly 42 may include a lens mold, including a first mold section 43 having a first lens defining surface 44 and a second mold section 45 having a second lens defining surface 46. The first and second mold sections 43 and 45 define a lens shaped cavity 8 between the first and second lens defining surfaces 44 and 46 when the first mold section 43 and the second mold section 45 are assembled together.

Turning now to FIG. 7B, a polymerizable composition 49 is provided in the lens shaped cavity 48. The polymerizable composition 49 can be understood to be a lens precursor composition. The polymerizable composition 49 can be a composition including one or more monomeric components suitable for producing contact lenses. The polymerizable composition 49 can be provided in the lens shaped cavity 48 by a number of different methods, for example, by injecting, dispensing, or otherwise introducing a polymerizable composition 49 into the lens shaped cavity.

Ophthalmic lenses manufactured using the present systems and methods may include ophthalmic lenses made from biocompatible, non-hydrogel materials or components. Examples of non-hydrogel materials include, and are not limited to, acrylic polymers, polyolefins, fluoropolymers, silicones, styrenic polymers, vinyl polymers, polyesters, polyurethanes, polycarbonates, cellulosics, proteins including collagen-based materials and the like and mixtures thereof. Preferably, for the manufacture of contact lenses in accordance with the present disclosure, the polymerizable composition comprises a formulation comprising one or more silicon-containing monomers and/or silicone-containing macromers.

A haptic configured for inclusion within a contact lens or other lens assembly or optical appliance can be flexible or rigid, and can embody material that can change curvature or shape in response to an applied force. The haptic can be formed of the same or different material than the contact lens into which it is incorporated and the haptic can be assembled prior to embedding within a contact lens and retained within the lens during further processing and manufacturing, or the haptic can be formed along with the creation of the lens. Further, as stated, the haptic can assume a myriad of shapes, and embody various features. In one aspect, the haptic can be transparent and can have the same refractive index as material surrounding the haptic. In other aspects, the haptic can be rotationally symmetric or asymmetric, variable in thickness or shapes and angled, or it can assume omega, square, oval, elliptical or other shapes, define a generally ribbon shape with overlapping ends, ends configured with springs or other flexible structure, or define other configurations where end points, portions or gaps can be manipulated via applied forces to change the shape of the haptic.

The haptic adapted for incorporation into a lens can be configured to bound an area that is occupied by one or more of a polymer or other flexible solid, air or fluid. Such bounded material or area is to be sufficiently flexible to provide desired curvature or thickness adjustments. One or a plurality of haptics can be incorporated within a lens to achieve the desired effect, and each of concentrically arranged, overlapping, arrays, and discrete placement of one or varied sizes of haptics are contemplated. Additionally, one or more haptics can have no gaps between end portions or alternatively can define a discontinuous structure including a single gap between adjacent end portions, or there can be multiple breaks and gaps formed in the haptic between each of which is configured structure responsive to electromagnetic energy. One or more haptics can also be planar or non-planar, have differing thicknesses or shape variations, and one or more haptic can be embedded at various angles within a lens.

Figure 8:
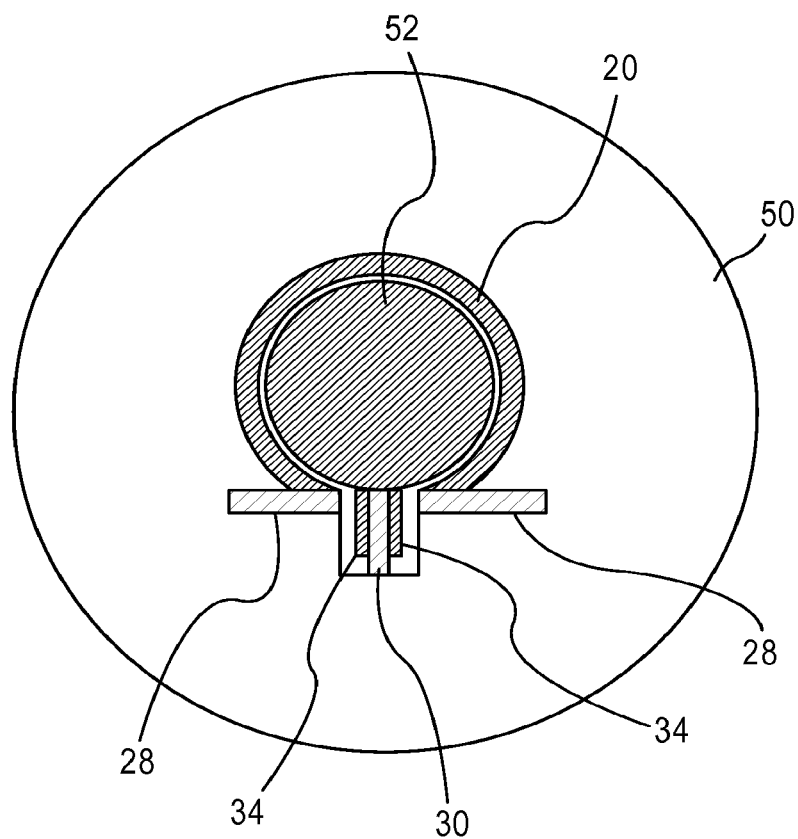
FIG. 8 is a front view, depicting a contact lens with an embedded haptic assembly.
Figure 9A:
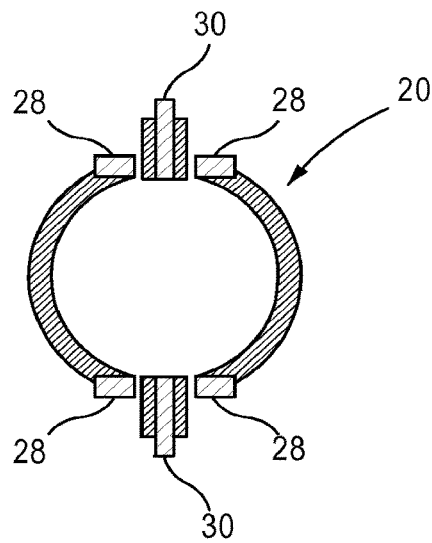
FIGS. 9A-D are front views, depicting alternative approaches to haptic assemblies.
Figure 9B:
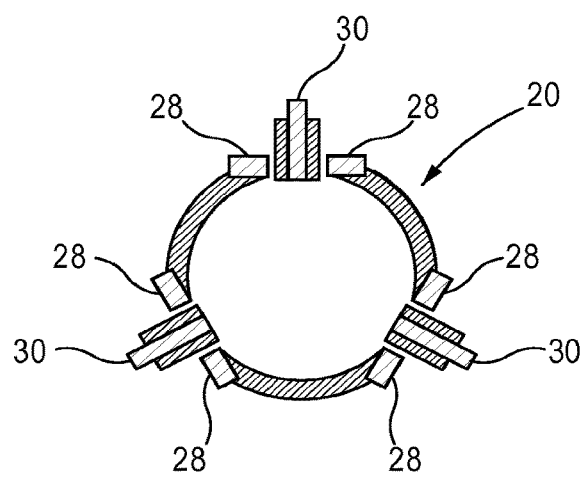
Figure 9C:
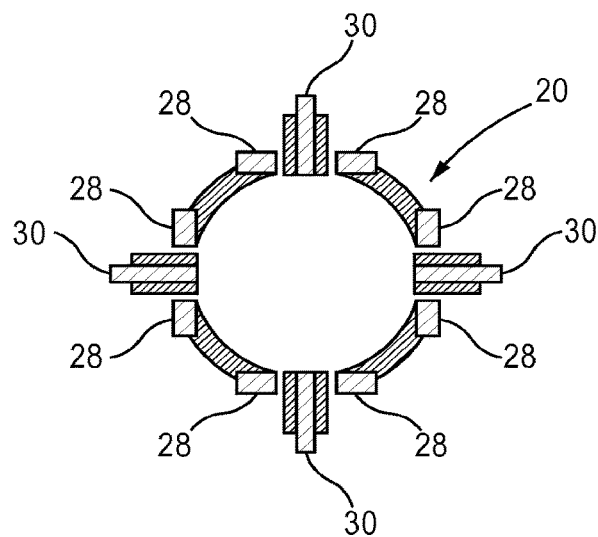
Figure 9D:
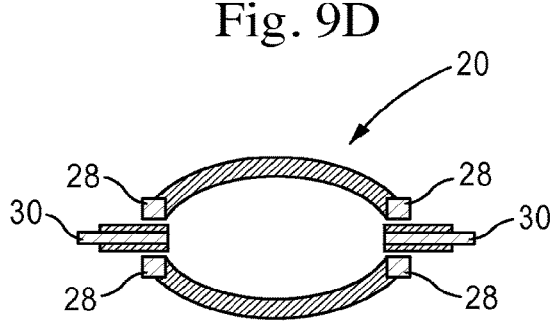

Turning to FIG. 8, there is shown a contact lens 50 embodying one particular form of a haptic 20 for adaptively tuning the lens by modifying the material bounded 52 by the haptic 20. Although shown defining an opaque structure, it is of course contemplated that portions of the haptic 20 can be created from transparent material. It is also contemplated that the haptic assembly be placed outside of the optical zone of a contact lens 50 into which it is embedded or associated with a lens, and can include a portion or portions interconnected or in communication with other electrical components. The haptic 20 is adapted to change the shape and/or thickness of the lens 50 with which it is it is associated to refract and focus light for vision correction. As above, the shape of the haptic 20 can embody a generally omega structure having a generally circular portion and a pair of opposing flat end portions. A gap exists between the end portions. In contemplated embodiments, the haptic 20 can be formed from a polymer, elastomer, silicone, silicone hydrogel, or other transparent flexible or rigid material.

Moreover, an electromagnet 30 can be positioned within the gap and adapted to mechanically deform the haptic 20. Using the electromagnet, the end portions 28 are attracted to or repelled from each other, changing the surface curvature, thickness, and dioptric power of the material or substance 52 bounded by the haptic 20. The electromagnet can be adapted to displace the end portions 28 to one or a plurality of preset positions. It is contemplated that in one approach, when the haptic is deformed it is positioned, shaped and forced such that the radius of curvature only affects the lens surface closest to the light source, as the opposing lens surface is adjacent to and formed along the surface of the eye.

As stated, electromechanical force can be applied to the end portions 28 of the haptic to cause deformation. Here, power is only required when changing states, and can range between 1-300 mW. No power is needed once a state has been changed, further reducing the power requirements when compared to the prior art. In an alternative embodiment, one or a plurality of piezoelectric motors can be used to cause the mechanical deformation of the haptic. In a further alternative embodiment, a memory shape alloy can be used to cause the mechanical deformation. In yet further alternative embodiments, electrostatic energy can be used to cause the mechanical deformation, a DC/AC motor can be employed, or a thermal actuator can cause the desired deformation.

Furthermore, as shown in FIGS. 9A-D and as stated above, the haptic can assume a myriad of shapes. Additionally, there can be multiple breaks or gaps in the haptic, one or more of which are configured with an electromagnet or other structure adapted to change the dimension of the gap. In this way, the extent to which the area bounded by the haptic can be modified in shape and/or thickness to a desired degree by providing multiple controls. This can provide infinite possibilities for optical correction including spheric, aspheric, toric, multifocal and wave front alternation control, and the like.

Figure 10A:
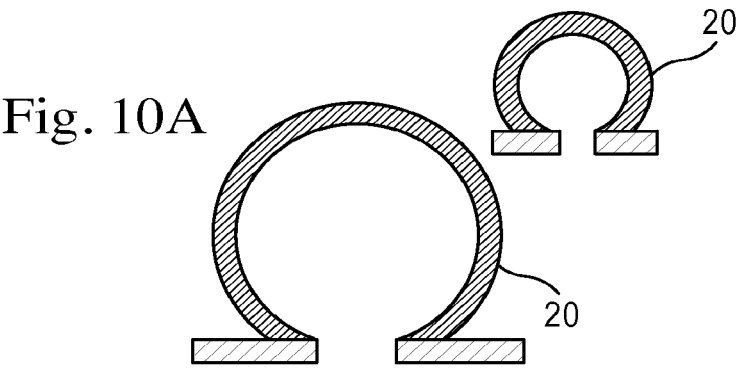
FIG. 10A-C are front views, depicting various alternative approaches to arrangements of multiple haptics.
Figure 10B:
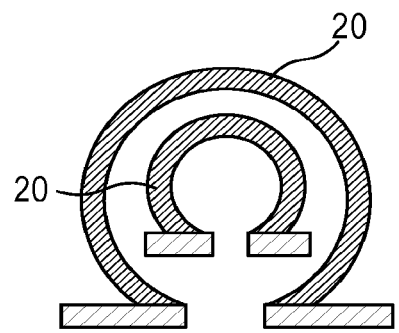
Figure 10C:
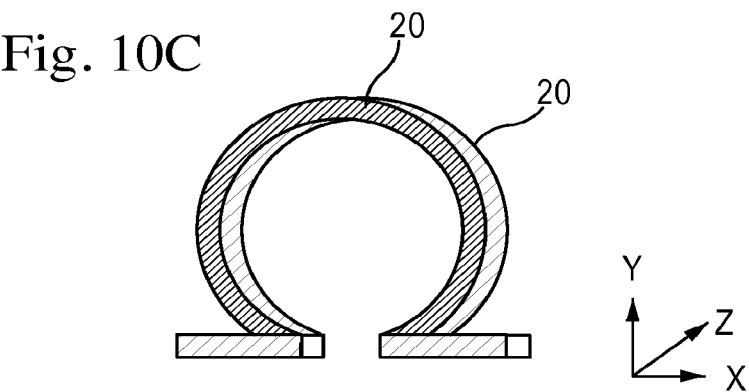
Figure 11:
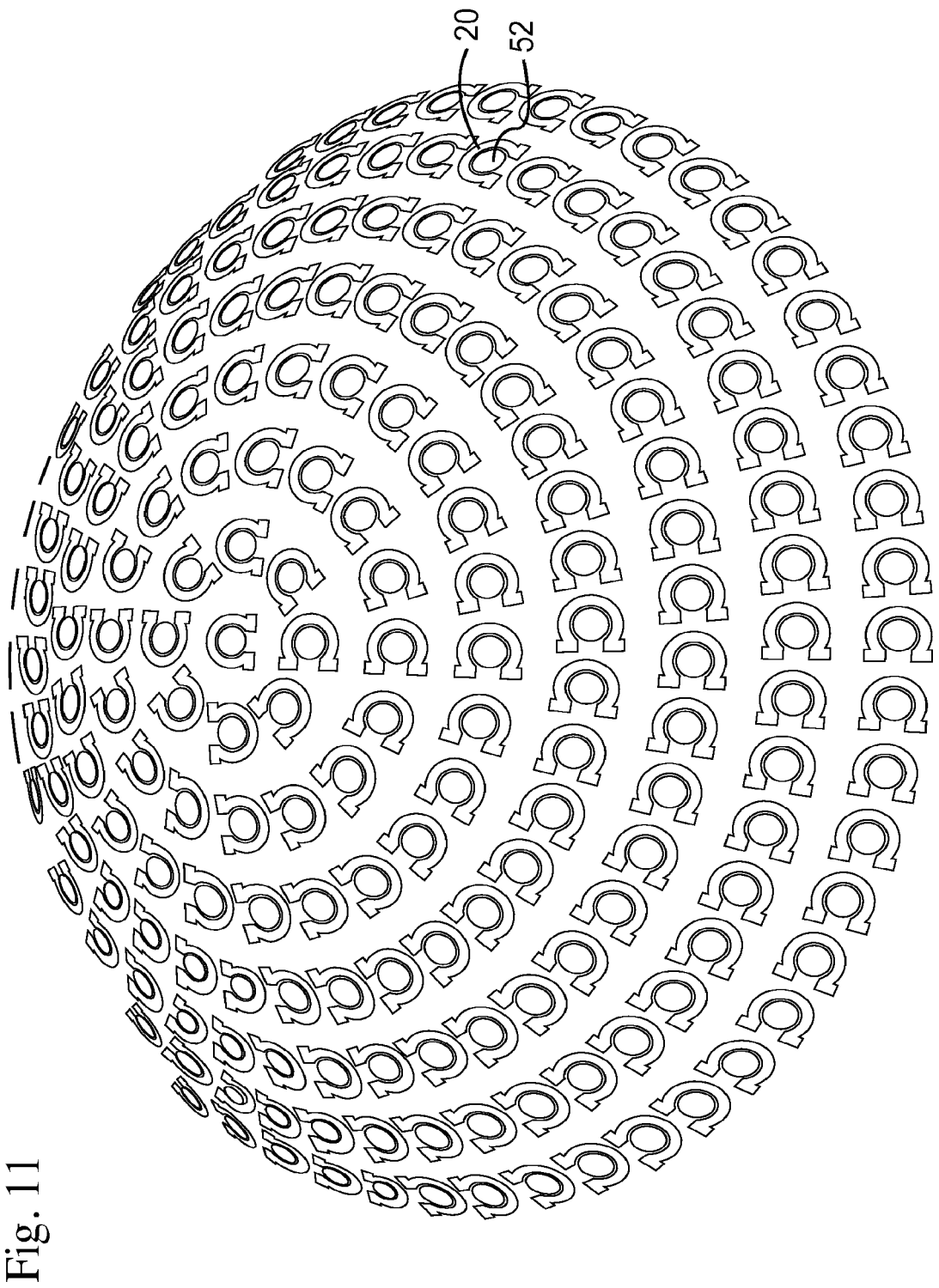
FIG. 11 is a front view, depicting a hemispherical array of haptics.

In alternative embodiments, a plurality of haptics are arranged and utilized in combination to provide varying effects for the user (See FIGS. 10A-C). A first approach (FIG. 10A) includes first and second haptics 20 having different sizes, where for example, the first haptic provides vision correction and the second provides zoom functionality. A second approach (FIG. 10B) can involve first and second haptics 20 arranged concentrically, and configured to provide desired zoom functionality. In a third approach, first and second haptics 20 are displaced in the z-axis to provide zoom functionality. Multiple haptics may also be used when different types of results are required such as long distance and short distance effects. For example, as shown in FIG. 11, a hemispherical array of haptics 20 can be embedded within a lens to create desired optical effects.

Figure 12:
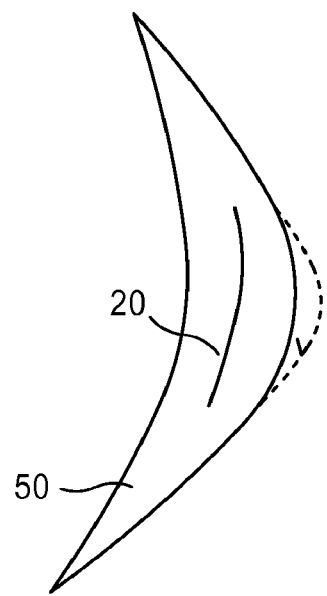
FIG. 12 is a side view, depicting the shape changing effect of a lens incorporating a haptic.
Figure 13:
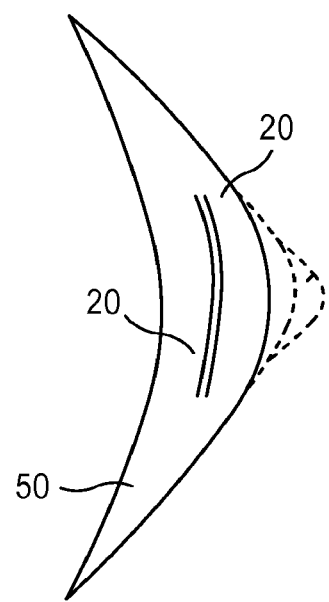
FIG. 13 is a side view, depicting shape changing effects of a lens incorporating a plurality of haptic assemblies.

Resultant self-focusing or adaptively tuning of a lens is illustrated in FIGS. 12 and 13. For example, a single haptic 20 can be placed within a lens 50 and energy can be applied to cause the lens 50 to change shape and/or thickness. Multiple haptics 20 (FIG. 13) can also be employed to achieve desired modification of a lens 50.

In order to create a lens embodying adaptive features, a first step of manufacture can involve creating the haptic or a plurality of haptics for embedding within a lens. The haptic may utilize the aforementioned omega shape, although any suitable shape may be used so long as the deforming of the lens provides adaptive focus. In the preferred embodiment, the lens assembly is adapted to withstand high temperatures commensurate with the lens material curing process.

The selected haptic or plurality of haptics can be placed directly onto a contact lens mold member, preferably the female mold member, or first (anterior) contact lens mold member. The placement can occur robotically and be coupled with a means of centering the assembly and structure or a means of controlling the depth of the assembly during the filling of the mold with a lens precursor material (See FIG. 14), which can be a polymerizable hydrogel or silicone hydrogel lens precursor composition.

Figure 14:
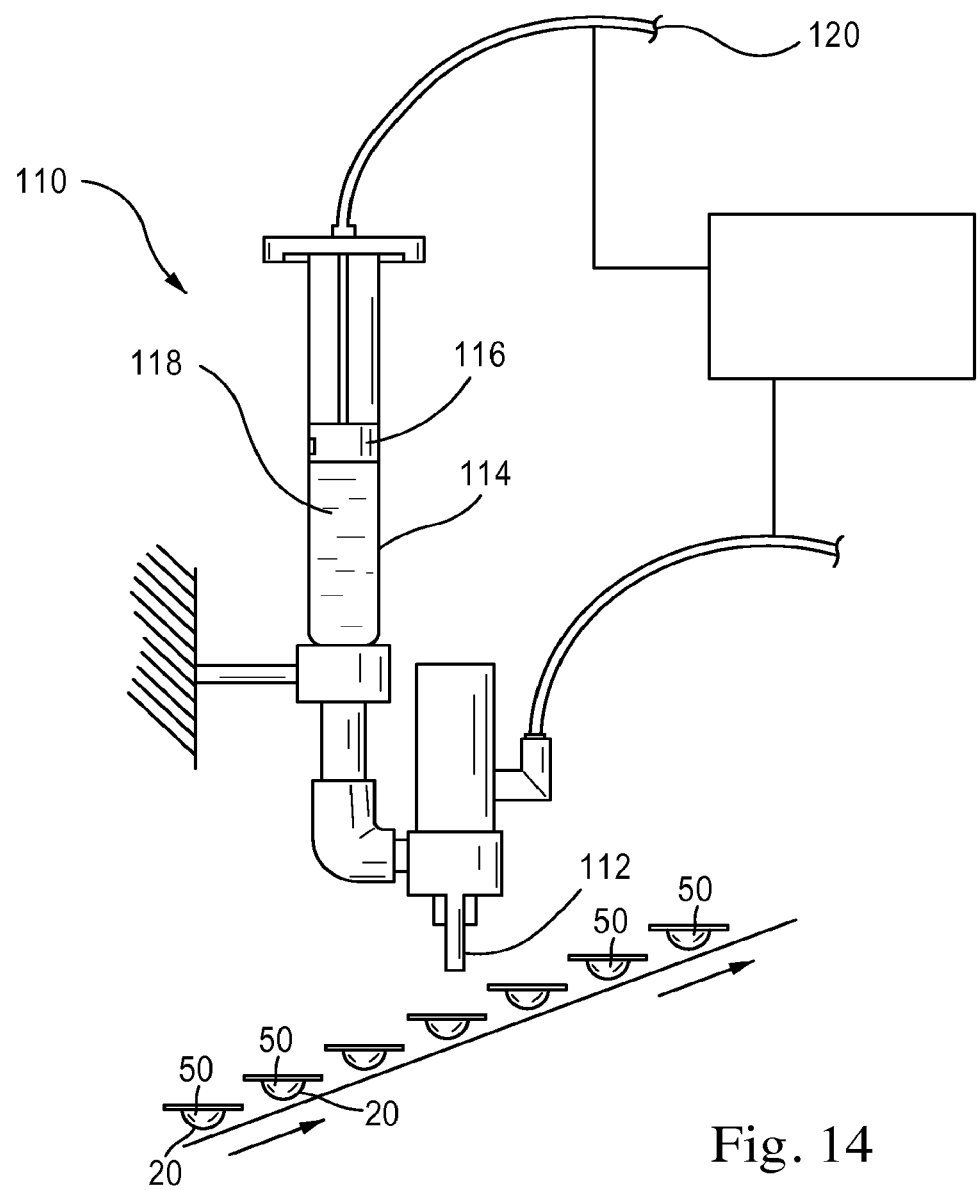
FIG. 14 is a side view, depicting one approach to contact lens manufacturing.

In one approach to manufacture, prior or subsequent to precise placement of the component on the concave surface of the female mold half 45, the lens precursor composition is placed on the concave surface of the first mold section. The composition can be placed on the concave surface using any conventional technique or device. However, in certain embodiments, the composition is placed on the concave surface using an automated dispensing apparatus, as shown in FIG. 14. In one approach, the automated dispensing apparatus 110 includes a dispensing tip 112 and a hollow body 114 containing the composition 118. A piston 116 is located in the body 114 to direct the composition from the dispensing tip 112. Movement of the piston 116 and the dispensing of the composition 118 can be controlled using a pressurized gas delivered via a pumping device and a conduit 120. Thus, discrete and reproducible amounts of the composition can be dispensed onto the concave surface.

The lens precursor composition or lens formulation can include monomers, macromers, polymers, crosslinkers, initiators, diluents, tinting agents, UV absorbing agents, and the like.

After placing the lens precursor composition 118 on the concave surface of the mold section, and precise placement of the component, the method can include placing a second mold section on the first mold section so that the convex surface of the second mold section and the concave surface of the first mold section form a contact lens shaped cavity. The two contact lens mold members are thus placed in contact with one another to form a contact lens shaped cavity, with the polymerizable silicone hydrogel lens precursor composition and the selected component positioned within the contact lens shaped cavity. The combination of the first mold section and the second mold section located thereon is referred to as a contact lens mold assembly. The first and second mold sections 43, 45 of the mold assembly (See also FIGS. 7A-B) can be held together using a variety of techniques. For example, the mold sections can be held together by pressure applied to opposing plates contacting opposite sides of the mold assembly. Or, the mold sections can be held together by an interference fit between the first mold section and the second mold section. Or, the mold sections can be welded together.

The polymerizable compositions can then be polymerized by placing the contact lens mold assemblies in a curing oven, which may use heat or light (e.g., visible or UV light, or combinations thereof) and the like to form polymerized contact lens products. It is during manufacturing that the pre-defined geometric shapes, voids or spaces are created as is more fully described below. In approaches involving thermoplastic substrate material or other materials which do not undergo polymerization, the pre-defined geometric shapes, voids or spaces can be formed as a product of injection or other molding and curing.

The polymerization or curing of the polymer lens precursor composition is effective to form a hydrogel or silicone hydrogel contact lens. The polymerizing may involve moving the contact lens, or a plurality of contact lenses, through a curing system, (not shown) which includes a plurality of ultraviolet lamps that provide a substantially uniform and substantially constant exposure of the lens precursor composition to the ultraviolet radiation. In certain approaches, the polymerizing involves exposing the lens precursor composition to an intensity of ultraviolet radiation. Heat can also be employed in other approaches. The polymerizable lens precursor composition is thus cured to form a pre-extracted polymerized contact lens product.

The contact lens mold is then demolded, where the two mold members are separated. When separated, the polymerized contact lens product is exposed, and can reside on one of the mold halves. The pre-extracted polymerized contact lens product is next separated from the contact lens molds, or delensed. After delensing, the pre-extracted contact lens product can be washed to remove unreacted monomers, diluents, and the like.

In one particular approach, the delensed or separated contact lens product is optionally inspected for defects, and then contacted with a liquid. That is, the separated adaptive contact lens product including one or more haptics may be placed directly in a contact lens package and contacted with a contact lens packaging solution, or the separated contact lens product may be washed to remove residual materials prior to placement in the contact lens package. The washing step can be viewed as an extraction, and it may employ the use of liquids that include aqueous solutions, organic solvents, or combinations thereof. The contact lens package containing the contact lens and the packaging solution are then sealed and sterilized.

In one or more embodiments, there is provided an adaptive focus lens comprising a lens, a haptic associated with the lens, the haptic including moveable, flexible or collapsible portions, an area bounded by the haptic and energy activatable structure configured between the portions, the haptic containing or bounding a polymer or other material which is the same or different than that of the base lens material, wherein applying energy to the energy activatable structure causes the portions to move relative to each other. Moreover, there can be provided an adaptive focus lens that can include a haptic configured to modify the curvature or thickness of a lens, the haptic including a pair of end portions, an electromagnet positioned in a gap between the pair of end portions, wherein the electromagnet attracts or repels the end portions to modify the power and focal length of the lens. The lens assembly can further include a pair of opposing electromagnets positioned adjacent to each opposing end portion opposite the gap and adapted to further attract or repel the end portions. The haptic can also include an open state, a closed state, and a rest state, wherein the open state involves the electromagnet repelling the opposing end portions such that a diameter of the haptic increases, causing power to decrease, wherein the closed state further involves the electromagnet attracting the end portions such that the diameter decreases, causing power to increase, and wherein the rest state further involves the electromagnet neither attracting nor repelling the end portions such that the diameter does not change. The adaptive focus lens can include a plurality of haptics adapted to provide vision correction and zoom functionality, or to provide long distance optics and short distance optics. Further the adaptive focus lens can include first and second haptics wherein the first haptic provides zoom functionality and the second haptic provides vision correction.

One method of manufacturing an adaptive focus lens involves providing a haptic and embedding it within a lens, modifying the shape of the lens with an electromagnet positioned in a gap between end portions of the haptic, wherein the electromagnet attracts or repels the end portions thereby modifying the power and focal length of the elastic lens. The method can further include providing a pair of opposing electromagnets positioned adjacent to each end portion and being adapted to further attract or repel the end portions. The method can also involve providing the haptic with an open state, a closed state, and a rest state, wherein the haptic includes a variable diameter, wherein the open state further involves the electromagnet repelling the opposing end portions such that the diameter increases, causing power and focal length to decrease, wherein the closed state further involves the electromagnet attracting the end portions such that the diameter decreases, causing said power and focal length to increase, and wherein the rest state further involves the electromagnet neither attracting nor repelling the end portions such that the diameter does not change from a base state.

Furthermore a method of manufacturing contact lens with adaptive focus lens can involve forming a haptic for incorporation into a lens, placing the haptic within a first contact lens mold member, filling the first contact lens mold with a lens precursor material, enclosing the assembly and lens precursor material with a second contact lens mold member, forming a contact lens-shaped cavity, curing the contact lens assembly and lens precursor material to create a contact lens with adaptive focus lens, demolding said contact lens with adaptive focus lens, delensing said contact lens with adaptive focus lens, extracting said contact lens with adaptive focus lens, hydrating said contact lens with adaptive focus lens in an aqueous solution, and packaging said contact lens with adaptive focus lens, wherein said hydration of said contact lens with adaptive focus lens will cause the lens precursor material and adaptive contact lens assembly to expand in size.

Accordingly, there has been provided approaches to adaptively modify the focus of lenses. The disclosed apparatus and methods accomplish desired adaptively modifying the power and focal length of lenses, and contact lenses in particular. Furthermore, there are provided approaches to adaptively adjust curvature and/or thickness of lenses.

While the above description contains specific details regarding certain elements, sizes, and other teachings, it is understood that embodiments of the disclosure or any combination of them may be practiced without these specific details. Specifically, although shapes and orientations are designated in the above embodiments, any shape and orientation may be used so long as it adequately performs as intended. Moreover, various alternative approaches to accomplish applying energy or forces can also be employed. These details should not be construed as limitations on the scope of any embodiment, but merely as exemplifications of the presently preferred embodiments. In other instances, well known structures, elements, and techniques have not been shown to clearly explain the details of the disclosure.

Moreover, while this disclosure has been described with respect to various specific examples and embodiments, it is to be understood that the same is not limited thereto and that it can be variously practiced within the scope of the following claims.

What is claimed is:

1. An adaptive focus lens, comprising:
   a lens material;
   a haptic embedded within said lens material, the haptic including moveable portions, wherein the haptic defines a generally omega shape having a gap, wherein said gap is provided between said moveable portions;
   an area bounded by the haptic; and
   an electromagnetic actuator configured to cooperate with said moveable portions, said electromagnetic actuator positioned within said gap and configured to mechanically deform the haptic;
   wherein applying energy to said electromagnetic actuator causes said moveable portions to move relative to each other and provide a uniform force to the periphery of the haptic.

2. The adaptive focus lens of claim 1, wherein the lens is a contact lens.

3. The adaptive focus lens of claim 1, wherein moving said moveable portions cause said area bounded by the haptic to change shape or thickness.

4. The adaptive focus lens of claim 1, wherein moving said moveable portions results in modifying the power of said lens.

5. The adaptive focus lens of claim 1, wherein said electromagnetic actuator is an electromagnetic assembly.

6. The adaptive focus lens of claim 1, wherein the area bounded by the haptic comprises a polymer, air, or liquid.

7. The adaptive focus lens of claim 1, wherein the haptic is transparent.

8. The adaptive focus lens of claim 1, wherein the haptic is flexible.

9. The adaptive focus lens of claim 1, wherein the haptic is formed from the same material as a substrate material.

10. The adaptive focus lens of claim 9, wherein multiple haptics are embedded within said substrate.

11. The adaptive focus lens of claim 9, wherein multiple haptics of varying sizes are embedded within said substrate.

12. The adaptive focus lens of claim 9, wherein the haptic is formed separately and placed within a mold prior to the lens substrate.

13. The adaptive focus lens of claim 1, wherein the haptic has one or more pairs of end portions, between at least one pair of which is configured as an energy activatable structure.

14. The adaptive focus lens of claim 1, wherein the adaptive focus lens is incorporated into a nonmedical device.

15. The adaptive focus lens of claim 1, wherein the lens is one of an intraocular lens, an inlay, or an onlay, or is incorporated into a scope or camera or projector, or as part of a fiber optic assembly.

* * * * *